United States Patent [19]

Maurer

[11] 4,154,656
[45] May 15, 1979

[54] METHOD FOR DETERMINING THE FIBRINOGEN CONTENT OF PHYSIOLOGICAL LIQUID

[75] Inventor: Robert Maurer, Wattenheim, Fed. Rep. of Germany

[73] Assignee: Knoll A.G. Chemische Fabriken, Ludwigshafen, Fed. Rep. of Germany

[21] Appl. No.: 779,584

[22] Filed: Mar. 21, 1977

[30] Foreign Application Priority Data

Apr. 10, 1976 [DE] Fed. Rep. of Germany ....... 2615844

[51] Int. Cl.$^2$ ..................... C07G 7/026; G01N 33/16; G01N 31/14; A61K 35/58
[52] U.S. Cl. ............................... 195/103.5 R; 195/63; 195/68; 424/98
[58] Field of Search ..................... 195/62, 99, 103.5 R, 195/66 B, 66 R, 63, 68; 424/94, 98

[56] References Cited

U.S. PATENT DOCUMENTS

| 3,819,605 | 6/1974 | Holleman et al. | 424/98 |
| 3,849,252 | 11/1974 | Peres et al. | 195/103.5 R |
| 3,985,618 | 10/1976 | Innerfield | 195/103.5 R |
| 4,027,012 | 5/1977 | Antonini | 424/98 |
| 4,055,635 | 10/1977 | Green et al. | 424/94 |

OTHER PUBLICATIONS

Muzaffar et al., "Fibrin Formation and Effects of Dextran," *Pharmacodynamics,* vol. 78, 66831p (1973).

*Primary Examiner*—Thomas G. Wiseman
*Attorney, Agent, or Firm*—Curtis, Morris & Safford

[57] ABSTRACT

What is disclosed is an enzyme system cleaving fibrinogen, said system comprising a fibrinogenase and a water-soluble polysaccharide.

1 Claim, No Drawings

METHOD FOR DETERMINING THE FIBRINOGEN CONTENT OF PHYSIOLOGICAL LIQUID

The present invention relates to an enzyme system for cleaving fibrinogen and to methods for making and using the same.

Fibrinogenases are known in the art [cf. German DOS 2,128,257; German DOS 2,440.254; and Brit. J. Haemat. 13, 581 (1967)]. Their activity is measured in units such that one unit corresponds to that amount of enzyme which will clot 0.1 ml of 0.3% bovine fibrinogen solution in 240 ± 23 seconds at a pH of 7.5 and at 37° C. Among other uses, fibrinogenases are used in therapy for the treatment of chronic disturbances of the peripheral blood circulation.

Fibrinogenases are, as a rule, recovered from animal sources. Thus, for example, ancrod is obtained from the venom of the Malayan pit viper. The preparation of large amounts of fibrinogenase is, for this reason, considerably expensive.

It has now been found that the activity of fibrinogenases can be considerably elevated by the addition of certain amounts of polymeric substances. In this way, in practical applications, smaller amounts of enzyme can be employed.

Thus, a feature of the present invention is an enzyme system for cleaving fibrinogen, which system comprises a fibrinogenase and a water-soluble polysaccharide, as well as a method for the preparation of this enzyme system by the addition of the components to an aqueous solution. Further, the present invention relates to therapeutic compositions and diagnostics which contain the aforementioned enzyme system.

As water-soluble polysaccharides, dextrans are particularly useful, preferably those having a molecular weight of about 10,000–60,000 especially about 20,000–40,000. Further, water-soluble starch and hydroxyethyl starch come into consideration. The polysaccharide is added to the enzyme solution in an amount of 1–20 mg, preferably 10–20 mg, per enzyme unit. The addition of larger amounts of polysaccharide is possible, however the enzyme activity is no longer increased thereby.

The increase in activity of the fibrinogenase by the polysaccharide can be explained by an interchange effect of the molecules. It cannot at this time be plainly clarified if the two compounds form a kind of complex with each other or join together only loosely.

The novel fibrinogen-cleaving enzyme system permits a rational determination of the fibrinogen content of physiological liquids, for example, blood. The determination of the fibrinogen content in blood is important for diagnosis of hyper- and hypofibrinogenemia, for tests of liver function, and for the control of therapy with pharmaceutical agents which decrease the fibrinogen content of blood. One part of the test solution is mixed with one part of the fibrinogenase-polysaccharide solution containing about 1 to 10 units of enzyme per ml and the turbidity of the solution is compared with a standard. For analytic purposes, the enzyme need not be particularly purified. Thus, for example, snake venom which contains fibrinogenases can be employed directly.

Further, the novel enzyme system make possible the treatment of disturbances of the peripheral blood circulation with small amounts of enzymes, whereby the danger of the appearance of allergic or resistance phenomena is reduced. The enzyme system is employed in aqueous solution in a dosage of 5–50 units per patient per day.

A better understanding of the present invention and of its many advantages can be had by referring to the following specific examples, given by way of illustration.

EXAMPLE 1

Reagent for Determination of Fibrinogen Content (a) 1 ml of ancrod solution (prepared according to German Pat. No. 1,442,134) and containing 70 units of enzyme is mixed with 4 ml of a 10% dextran solution (molecular weight = 40,000) and 5 ml of a 0.9% NaCl solution.

(b) 0.2 mg of snake venom is taken up in 1 ml of 10% dextran solution.

EXAMPLE 2

Solution for Intravenous Application 0.5 ml portions of ancrod solution (prepared as in Example 1) are combined with 499.5 ml portions of a 10% dextran solution (molecular weight = 60,000) and filled into bottles.

The mixing of the sterile solution takes place under the protection of laminar-airflow.

EXAMPLE 3

Solution for Subcutaneous Application 1 ml portions of ancrod solution (prepared as in Example 1) are mixed with 9.0 ml portions of a 10% dextran solution (molecular weight = 40,000) under sterile conditions and filled into ampoules.

The activity of the novel fibrinogen-cleaving enzyme system was determined with the help of the following solutions:

(A) 0.3 mg fibrinogen in 100 ml of buffer (pH=7.5) which is 0.01 molar in tris-(hydroxymethyl)-aminomethane and 0.15 molar in NaCl;

(B) 1.4 units of ancrod in 10 ml of 0.9% NaCl solution;

(C) 1.4 units of ancrod in 10 ml of 0.9% NaCl solution which contains 1,000 mg of dextran (molecular weight = 60,000); and (D) 1.4 units of ancrod in 10 ml of 0.9% NaCl solution which contains 1,000 mg of dextran (molecular weight = 40,000).

(E) 1.4 units of ancrod in 10 ml of 0.9% NaCl solution which contains 1,000 mg of dextran (molecular weight = 20,000).

2 ml of solution B, C, and D, were respectively mixed with 1 ml of solution A and the clotting time was measured at 25° C. The following values were obtained:

| Mixture | | | Clotting Time |
| --- | --- | --- | --- |
| (A) | + | (B) | 597 Seconds |
| (A) | + | (C) | 43 Seconds |
| (A) | + | (D) | 6 Seconds |
| (A) | + | (E) | 25 Seconds |

From this it is evident that the enzyme effect is increased by a factor of 13–100 if a water soluble polysaccharide is added to the enzyme according to the invention. A dextran solution alone does not clot fibrinogen.

Similar results are obtained with the venoms of other vipers such as *Agkistrodon acutus, Bothrops atrox, Bothrops jararaca, Bothrops moojeni, Bothrops marajoensis, Bothrops asper, Bothrops pradoi, Crotalus adamanteus, Crotalus atrox, Trimeresurus flavoviridis, Viper aspis, Viper berus, Denisonia superba, Notechis scutatus,* and *Pseudechis porphyriacus.*

What is claimed is:

1. The method for determining the fibrinogen content of a physiological liquid, which comprises mixing one part of the physiological liquid with about one part of a solution of a fibrinogenase found in viper venom and a water-soluble dextran in a quantity to enhance the enzymatic activity said solution containing one to ten units of enzyme per milliliter, permitting turbidity to develop in the resulting mixture, and comparing the turbidity developed in the resulting mixture with that of a reference standard.

* * * * *